(12) United States Patent
Kim et al.

(10) Patent No.: US 10,189,021 B2
(45) Date of Patent: Jan. 29, 2019

(54) MICROFLUIDIC CHIP, MANUFACTURING METHOD THEREFOR AND ANALYSIS DEVICE USING SAME

(71) Applicant: NANOBIOSYS INC., Seoul (KR)

(72) Inventors: Sung Woo Kim, Seoul (KR); Jae Young Byun, Anyang-si (KR)

(73) Assignee: NANOBIOSYS INC., Seoul (KR)

( * ) Notice: Subject to any disclaimer, the term of this patent is extended or adjusted under 35 U.S.C. 154(b) by 175 days.

(21) Appl. No.: 15/325,293

(22) PCT Filed: Jun. 22, 2015

(86) PCT No.: PCT/KR2015/006320
§ 371 (c)(1),
(2) Date: Jan. 10, 2017

(87) PCT Pub. No.: WO2016/006842
PCT Pub. Date: Jan. 14, 2016

(65) Prior Publication Data
US 2017/0157606 A1    Jun. 8, 2017

(30) Foreign Application Priority Data

Jul. 10, 2014    (KR) .......................... 10-2014-0086758

(51) Int. Cl.
*B81B 1/00*    (2006.01)
*B81C 1/00*    (2006.01)
(Continued)

(52) U.S. Cl.
CPC ....... *B01L 3/502707* (2013.01); *B01L 3/5027* (2013.01); *B81B 1/00* (2013.01);
(Continued)

(58) Field of Classification Search
CPC ......... B01L 2200/0684; B01L 2200/10; B01L 2200/12; B01L 2300/0636;
(Continued)

(56) References Cited

U.S. PATENT DOCUMENTS

| 7,233,000 B2 | 6/2007 | Nassiopoulou et al. |
| 7,842,240 B2 | 11/2010 | Yamamoto et al. |

(Continued)

FOREIGN PATENT DOCUMENTS

| CN | 102348506 A | 2/2012 |
| CN | 102614948 A | 8/2012 |

(Continued)

*Primary Examiner* — Jennifer Wecker
(74) *Attorney, Agent, or Firm* — Novick, Kim & Lee, PLLC; Sang Ho Lee

(57) ABSTRACT

According to embodiments of the present invention, a microfluidic chip, a manufacturing method therefor and an analysis device using the same are provided. The microfluidic chip comprises: a substrate comprising an inflow part through which a fluid flows in, a fluid channel through which the fluid moves and an outflow part through which the fluid flows out; and a film attached to the substrate to protect at least one of the inflow part, the outflow part and the fluid channel from the outside, wherein the inflow part and the outflow part are implemented by penetrating through the surface of the substrate, and the fluid channel can be implemented by being sunk from the surface of the substrate.

18 Claims, 3 Drawing Sheets

(51) Int. Cl.
*B01L 3/00* (2006.01)
*B81B 7/00* (2006.01)
*G01N 15/06* (2006.01)
*G01N 27/447* (2006.01)

(52) U.S. Cl.
CPC ............ *B81B 7/00* (2013.01); *B81C 1/00071* (2013.01); *B01L 3/502715* (2013.01); *B01L 2200/0684* (2013.01); *B01L 2200/10* (2013.01); *B01L 2200/12* (2013.01); *B01L 2200/141* (2013.01); *B01L 2300/041* (2013.01); *B01L 2300/048* (2013.01); *B01L 2300/0636* (2013.01); *B01L 2300/0681* (2013.01); *B01L 2300/0816* (2013.01); *B01L 2300/0867* (2013.01); *B01L 2300/0887* (2013.01); *B01L 2300/12* (2013.01); *B81B 2201/058* (2013.01); *B81B 2203/0338* (2013.01); *G01N 15/06* (2013.01); *G01N 27/44743* (2013.01)

(58) Field of Classification Search
CPC ..... B01L 2300/0816; B01L 2300/0887; B01L 2300/12; B01L 3/502707; B01L 3/5027; B01L 3/502715; B01L 2200/141; B01L 2300/041; B01L 2300/048; B01L 2300/0681; B01L 2300/0867; B01L 2300/0877; B81B 1/00; B81B 2201/058; B81B 2203/0338; B81B 7/00; B81C 1/00071; G01N 15/06; G01N 27/44743; G01N 27/44791
See application file for complete search history.

(56) References Cited

U.S. PATENT DOCUMENTS

| | | | |
|---|---|---|---|
| 2003/0116813 A1* | 6/2003 | Benzel | B81C 1/00595 257/414 |
| 2004/0045891 A1* | 3/2004 | Gilbert | C30B 29/58 210/321.65 |
| 2004/0108479 A1* | 6/2004 | Gamier | B81B 3/0035 251/129.01 |
| 2012/0070878 A1 | 3/2012 | Fink et al. | |
| 2013/0140181 A1 | 6/2013 | Quake et al. | |

FOREIGN PATENT DOCUMENTS

| | | |
|---|---|---|
| CN | 103118784 A | 5/2013 |
| CN | 203663854 U | 6/2014 |
| JP | 2004-202613 A | 7/2004 |
| JP | 2006-255584 A | 9/2006 |
| JP | 2007-136379 A | 6/2007 |
| JP | 2008-232939 A | 10/2008 |
| JP | 2009-109249 A | 5/2009 |
| JP | 2009-236555 A | 10/2009 |
| JP | 2013-007592 A | 1/2013 |
| KR | 10-0445744 B1 | 8/2004 |
| KR | 10-2008-0085898 A | 9/2008 |
| KR | 10-1244285 B1 | 3/2013 |
| KR | 10-2013-0066138 A | 6/2013 |
| WO | 2007/125642 A1 | 11/2007 |
| WO | 2010/038897 A1 | 4/2010 |

* cited by examiner

MICROFLUIDIC CHIP, MANUFACTURING METHOD THEREFOR AND ANALYSIS DEVICE USING SAME

TECHNICAL FIELD

The present invention relates to a microfluidic chip, a manufacturing method thereof and an analysis device using the same, and more specifically, to a microfluidic chip having a fluid channel formed on the surface of a substrate, a manufacturing method thereof and an analysis device using the same.

The present invention has been derived from a research sponsored by Industrial fusion source technology development business of Ministry of Trade, Industry and Energy [Project number: 10042924, Project name: Development of a prototype of a system for automatically screening optimum stem cell culture conditions at a high speed using a complex gradient (nano-structure gradient-concentration gradient) technique].

BACKGROUND ART

A microfluidic chip has a function of simultaneously executing various experiment conditions by discharging fluid through a microfluidic channel. Specifically, the microfluidic channel is created using a substrate (or a chip material) of plastic, glass, silicon or the like, and after moving a fluid (e.g., a liquid sample) through the channel, for example, separation of a sample, mixture, synthesis and quantitative analysis of cells, observation of cell proliferation and the like may be performed in a chamber of the microfluidic chip. The microfluidic chip is also referred to as a "lab-on-a-chip" because experiments conducted in a laboratory of the prior art were carried out in a small chip.

The microfluidic chip may create an effect of saving cost and time in the pharmaceutical field, biological engineering field, medical field, biomedical field, food sector, environmental field, fine chemistry field and the like, and in addition, it may enhance accuracy, efficiency and reliability. For example, since doses of expensive reagents used for culture, proliferation and differentiation of cells can be reduced remarkably by using the microfluidic chip compared to existing methods, cost can be saved considerably. Furthermore, in conducting an analysis on a biological sample such as a protein, a DNA, a cell, a neuron, an enzyme, an antibody or the like, the amount of samples used in the analysis is much smaller than that of the conventional method, and images can be analyzed using the samples, and thus the amount of samples used or consumed for analysis and the time required for analyzing the samples can be reduced.

In relation to this, FIG. 1 shows an exploded view of a portion of an exemplary microfluidic chip of the prior art.

As shown in the figure, the exemplary microfluidic chip 100 of the prior art may include a plurality of first channels 110 and a plurality of second channels 120. In the exemplary microfluidic chip 100, a fluid flowing through the plurality of first channels 110 is mixed with a fluid flowing through the plurality of second channels 120, and the channels may be formed in different layers to facilitate flow and mixture of the fluids.

To this end, the microfluidic chip of the prior art is manufactured by bonding at least two substrates (or layers) on which the channels are formed respectively. However, according to such a manufacturing method, since a plurality of substrates should be bonded to each other after the channels are formed on the substrates, there is a problem of alignment between the substrates. That is, considerable time and cost are required in the process of bonding the substrates when the microfluidic chip is manufactured. Furthermore, time and cost are also required to manufacture the two layers of substrates (i.e., two substrates) (e.g., through an injection molding process or the like). That is, the microfluidic chip of the prior art has a problem in the manufacturing process from the aspect of time and cost and also has a problem of degrading precision of the chip.

Accordingly, a microfluidic chip, a manufacturing method thereof and an image analysis device using the same are required to solve these problems.

DISCLOSURE OF INVENTION

Technical Problem

Therefore, the present invention has been made in view of the above problems, and it is an object of the present invention to provide a microfluidic chip, a manufacturing method thereof and an analysis device using the same, which can solve the bonding and alignment problem between the substrates by implementing a fluid channel formed on the substrates.

Technical Solution

According to one embodiment of the present invention, a microfluidic chip is provided. The microfluidic chip includes: a substrate including an inflow part through which a fluid flows in, a fluid channel through which the fluid moves and an outflow part through which the fluid flows out; and a film attached to the substrate to protect at least one of the inflow part, the outflow part and the fluid channel from the outside, in which the inflow part and the outflow part may be implemented to penetrate the surface of the substrate, and the fluid channel may be implemented to be depressed from the surface of the substrate.

According to one embodiment of the present invention, an analysis device is provided. The analysis device may include: the microfluidic chip; and a light detection module implemented to detect an optical signal emitted from a light measurement area of the microfluidic chip by radiating light on the microfluidic chip to measure a reaction product in the microfluidic chip.

According to one embodiment of the present invention, a method of manufacturing a microfluidic chip is provided. The method may include the steps of: forming a substrate including an inflow part through which a fluid flows in, a fluid channel through which the fluid moves and an outflow part through which the fluid flows out; and attaching a film to the surface of the substrate to protect at least one of the inflow part, the outflow part and the fluid channel from the outside, in which the step of forming a substrate may be performed by implementing the fluid channel by depressing at least a portion of the top surface or the bottom surface of the substrate from the surface of the substrate and implementing the inflow part and the outflow part to penetrate the surface of the substrate.

Advantageous Effects

According to the present invention, unlike a conventional technique of bonding a plurality of substrates, precision of a microfluidic chip can be improved and a defect rate can be lowered by preventing errors in a process related to alignment and the like.

In addition, according to the present invention, since the microfluidic chip is manufactured simply by boding a substrate and a film, the manufacturing process is simple and cost-effective.

In addition, according to the present invention, the overall size and weight of the microfluidic chip can be reduced, and therefore, convenience of a user and economic efficiency can be enhanced.

In addition, according to the present invention, bubbles in a fluid can be effectively removed to the outside of a light measurement area using only a structure formed in the microfluidic chip, without an additional chemical process or additional equipment such as a pump driving device, an ultrasonic device a membrane or the like.

In addition, according to the present invention, although the microfluidic chip is extremely miniaturized, a plurality of small amount reaction products can be simultaneously measured in a speedy and accurate way without a problem of reduction and non-uniformity of optical signal sensitivity.

BRIEF DESCRIPTION OF THE DRAWINGS

Brief description on each drawing is provided to further understand the drawings referenced in the detailed description of the present invention.

BEST MODE FOR CARRYING OUT THE INVENTION

Figure 1:
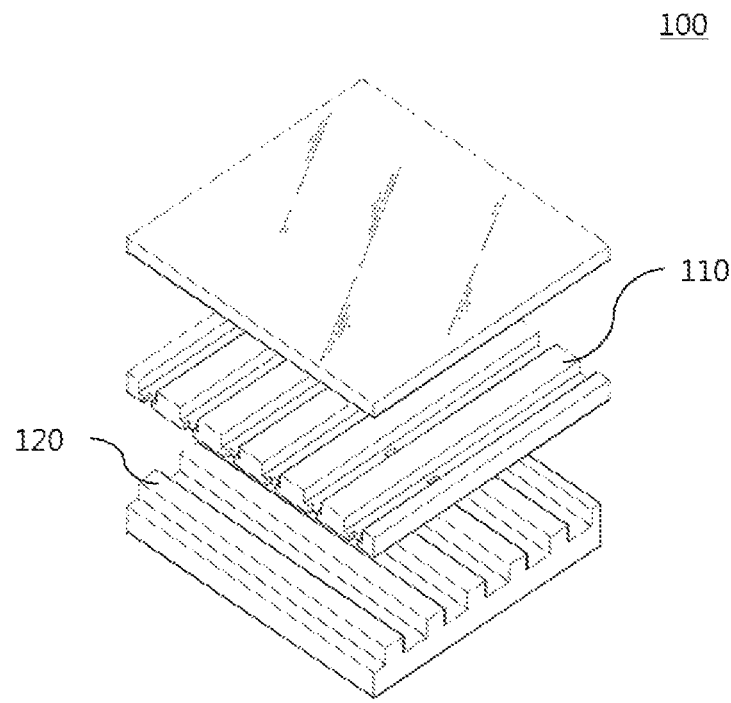
FIG. 1 shows an exploded view of a portion of an exemplary microfluidic chip of the prior art.

Hereafter, embodiments according to the present invention will be described with reference to the accompanying drawings. In assigning reference numerals to constitutional components of each drawing, it should be noted that like constitutional components will have like reference numerals if possible although they are shown in different drawings. In addition, in describing the embodiments of the present invention, if specific description of already known constitution or functions related to the present invention may hinder understanding of the present invention, detailed description thereof will be omitted. In addition, although the embodiments of the present invention will be described hereinafter, the technical spirits of the present invention will not be limited or restricted thereto and may be modified by those skilled in the art and diversely embodied.

Throughout the specification, when an element is connected to another element, it includes a case of indirectly connecting the elements with intervention of another element therebetween, as well as a case of directly connecting the elements. In addition, the concept of including a constitutional element means further including another constitutional element, not excluding another constitutional element, as far as an opposed description is not specially specified.

Figure 2:
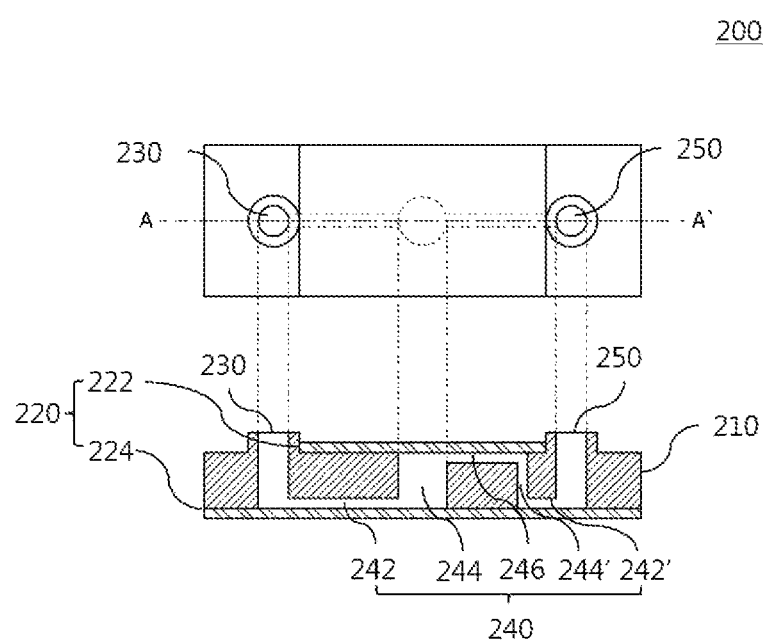
FIG. 2 shows a microfluidic chip according to an embodiment of the present invention.

FIG. 2 shows a microfluidic chip according to an embodiment of the present invention. Specifically, the upper part of FIG. 2 shows a plan view of the microfluidic chip 200, and the lower part of FIG. 2 shows a cross-sectional view of A-A' direction of the microfluidic chip 200.

Referring to FIG. 2, the microfluidic chip 200 may include a substrate 210 and a film 220 bonded to the substrate 210.

The substrate 210 is a base of the microfluidic chip 200 and may include an inflow part 230 through which a fluid flows in, a fluid channel 240 through which the fluid moves and an outflow part 250 through which the fluid flows out. The inflow part 230, the fluid channel 240 and the outflow part 250 of the substrate 210 may be formed to be depressed from the surface (i.e., the top surface and the bottom surface) of the substrate 210 or to penetrate the substrate 210.

The substrate 210 may be implemented using a material selected from a group configured of polydimethylsiloxane (PDMS), cycle olefin copolymer (COC), polymethylmethacrylate (PMMA), polycarbonate (PC), polypropylene carbonate (PPC) or polyether sulfone (PES), polyethylene terephthalate (PET), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT) or fluorinated ethylenepropylene (FEP) and a combination thereof. In addition, at least a portion of the substrate 210 may be implemented using a light transmissive material, e.g., perfluoralkoxyalkane (PFA) or the like, according to embodiments. However, the materials of the substrate 210 are only exemplary, and various materials can be used according to embodiments to which the present invention is applied.

The film 220 may be bonded on the surface of the substrate 210. Specifically, the film 220 may be configured of a first film 222 bonded on the top surface of the substrate 210 and a second film 224 bonded on the bottom surface of the substrate 210, and since at least some of the inflow part 230, the outflow part 250 and the fluid channel 240 of the substrate 210 are insulated from the outside by bonding the first film 222 and the second film 224 like this on the top surface and the bottom surface of the substrate 210, the microfluidic chip 200 may be protected from contamination, damage and the like caused by foreign materials, and at the same time, the microfluidic chip 200 may perform a function of flowing or maintaining the fluid.

Instead of a different substrate that has a similar or equal material as substrate 210, a relatively thin film 220 is attached on the surface of the substrate 210, which simplifies the bonding process and helps miniaturization and weight reduction of the microfluidic chip 200. At least a portion of the film 220 may be a transparent or opaque material. In addition, the film 220 may be a gas permeable film for a gas such as oxygen, carbon dioxide or the like. Such a configuration of the film 220 is only exemplary, and the configuration of the film may be diversified according to embodiments to which the present invention is applied, i.e., according to ingredients of a sample used in the microfluidic chip 200 or the purpose of research.

According to the microfluidic chip 200 above, a fluid such as a sample reagent, a sample material or the like is injected through the inflow part 230 and flows through the fluid channel 240. Here, the fluid channel 240 may include lower fluid channels 242 and 242' formed on the bottom surface of the substrate 210, an upper fluid channel 246 formed on the top surface of the substrate 210, and via holes 244 and 244' connecting the lower fluid channels 242 and 242' and the upper fluid channel 246. More specifically, the fluid injected through the inflow part 230 flows through the lower fluid channel 242, the via hole 244, the upper fluid channel 246, the via hole 244' and the lower fluid channel 242' in order. In addition to moving and maintaining the fluid, various operations can be performed on the fluid in the fluid channel 240. For example, the via hole 244 may connect the lower fluid channel 242 and the upper fluid channel 246, and in addition, it may function as a predetermined reaction channel or reaction chamber. That is, since the via hole 244 secures a sufficient space as large as to function as a reaction channel or a reaction chamber, unlike the via hole 244' for flowing the fluid, a predetermined reaction such as mixture, synthesis, quantitative analysis of cells, observation of cell proliferation and the like or analysis and observation of the reaction may be accomplished through the reaction channel or the reaction chamber implemented through the via hole 244. However, utilization of the via hole 244 is only exemplary, and the fluid channel 240 may not include a via hole functioning as a reaction channel or a reaction chamber according to embodiments to which the present invention is applied. The fluid that has passed through the fluid channel 240 may flow out to the outside of the microfluidic chip 200 through the outflow part 250.

Like this, since the fluid channel 240, which may require a complex fluid flow path and a relatively wide area, is formed by making different surfaces on the substrate 210, miniaturization of the microfluidic chip 200 and simplification of the process can be accomplished. Particularly, the bonding and alignment problem between the substrates generated by bonding a plurality of substrates can be solved.

In an embodiment, the fluid channel 240 may include a branch channel and/or a combined channel. The branch channel splits a certain channel into a plurality of different channels, and a fluid flowing through the certain channel may be split into a plurality of fluids having the same properties. The combined channel combines a plurality of channels into one channel, and a plurality of fluids flowing through a plurality of channels may be combined into one fluid. The branch channel and/or the combined channel may be implemented by an upper fluid channel and/or a lower fluid channel of the fluid channel 240. Particularly, the fluid channel 240 may include, as described below in more detail, a concentration gradient channel implemented by combining the branch channel and the combined channel. Here, the concentration gradient channel may provide concentration gradients of a fluid by forming diverse paths capable of combining and splitting the fluid passing through the channel while repeating a process of splitting one or more channels into one or more channels and forming a new channel by combining some of the split channels.

In addition, according to embodiments, the fluid channel 240 may further include, as described below in more detail, a bubble removing part (see 310 of FIG. 3 and 410 of FIG. 4) for preventing bubbles contained in the fluid from being positioned in a predetermined area. The bubble removing part may be used for a variety of purposes at various positions in the fluid channel 240. For example, the fluid channel 240 may include a light measurement area for measuring products of various reactions (e.g., PCR reaction or the like) performed in the fluid channel 240, and in this case, the bubble removing part may be formed to prevent bubbles contained in the fluid from being positioned in the light measurement area.

In addition, according to embodiments, surface treatment may be performed on a portion (preferably, at least one of the inflow part 230, the fluid channel part 240 and the outflow part 250) of the surface of the substrate 210. For example, a material of a silane family, Bovine Serum Albumin (BSA) or the like may be coated on the surface to prevent adsorption of DNA or protein, and the surface treatment may be performed according to various techniques publicized in the art.

In addition, according to embodiments, a separate cover means (not shown) is provided on the inflow part 230 and the outflow part 250 to prevent contamination of the inside of the microfluidic chip 200 through the inflow part 230 and the outflow part 250 or to prevent leakage or the like of the fluid injected in the microfluidic chip 200. Such a cover means may be implemented in a variety of shapes, sizes or materials.

The shape or the structure of the microfluidic chip 200 shown in FIG. 2 are only exemplary, and microfluidic chips of various shapes or structures may be used according to embodiments to which the present invention is applied.

Figure 3:
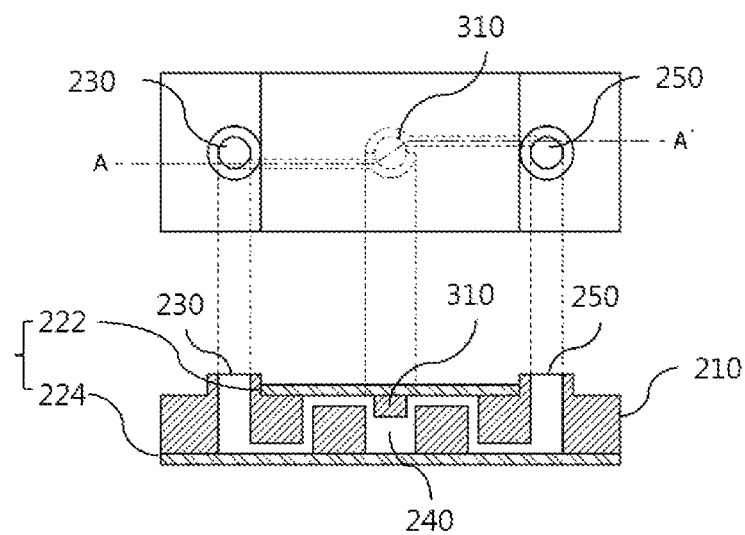
FIG. 3 shows a microfluidic chip according to another embodiment of the present invention.

FIG. 3 shows a microfluidic chip according to another embodiment of the present invention.

Specifically, the upper part of FIG. 3 shows a plan view of a microfluidic chip 300, and the lower part of FIG. 3 shows a cross-sectional view of A-A' direction of the microfluidic chip 300.

Referring to FIG. 3, the fluid channel 240 of the microfluidic chip 300 may include a bubble removing part 310. The bubble removing part 310 is an element for preventing bubbles contained in the fluid from being positioned in a predetermined area in the fluid channel 240 and may be formed to be protruded from the top inner surface of the substrate 210 toward the bottom.

The fluid channel 240 may include a light measurement area for measuring a product of a certain reaction performed in the fluid channel 240 (i.e., an area in the fluid channel 240, in which an optical signal emitted from the reaction product is detected), and at this point, the bubble removing part 310 may be formed to prevent bubbles contained in the fluid from being positioned in the light measurement area. Therefore, the bubble removing part 310 may remove the factors hindering detection of the optical signal sensed in the light measurement area. Specifically, since the bubble removing part 310 is protruded from the top inner surface of the substrate 210 toward the inside of the fluid channel 240, the bubbles contained in the fluid are pushed from the bubble removing part 310 to an area around the light measurement area (i.e., a flat area of the protruded portion of the bubble removing part 310) due to buoyancy and arranged in a space around the bubble removing part 310. That is, the bubbles are moved out from the light measurement area to the outside and do not affect sensitivity of the optical signal emitted from the reaction product existing in the light measurement area. Particularly, at least a portion of the substrate 210, i.e., the bubble removing part 310, is configured of a light transmissive material, and at least a portion may be configured to be included in the light measurement area, and accordingly, the optical signal generated from the reaction product in the light measurement area may pass through the bubble removing part 310 and may be emitted to the outside of the microfluidic chip without degradation of sensitivity. If the reaction product in the fluid channel 240 is measured using the microfluidic chip like this, sensitivity of the optical signal is considerably enhanced although the microfluidic chip is miniaturized extremely since it is not affected by the bubbles generated in the fluid channel 240, and thus a plurality of small amount reaction products can be simultaneously measured in a speedy and accurate way.

Using such a bubble removing part 310 is only exemplary, and the bubble removing part 310 may be utilized for a variety of purposes according to embodiments to which the present invention is applied. For example, the bubble removing part 310 may be used to remove bubbles contained in the fluid from the flow of the fluid while the fluid flows through the fluid channel 240.

The shape of the bubble removing part 310 shown in FIG. 3 is only exemplary and not limited thereto and may be diversely modified and applied according to embodiments of the present invention. For example, although the bubble removing part 310 of a cylindrical shape is shown in FIG. 3, a bubble removing part of another shape such as a square pillar or the like may be used.

Figure 4:
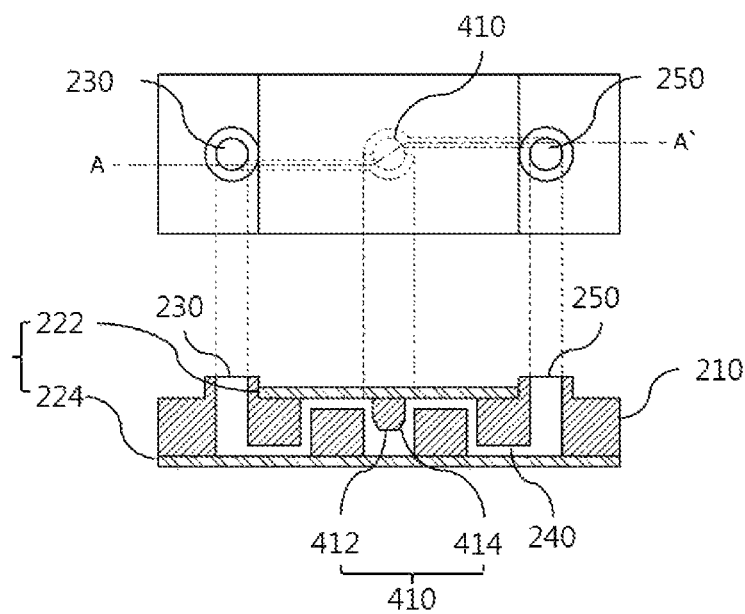
FIG. 4 shows a microfluidic chip according to an embodiment of the present invention.

FIG. 4 shows a microfluidic chip according to an embodiment of the present invention.

Specifically, the upper part of FIG. 4 shows a plan view of a microfluidic chip 400, and the lower part of FIG. 4 shows a cross-sectional view of A-A' direction of the microfluidic chip 400.

Referring to FIG. 4, a bubble removing part 410 may be configured of a flat surface 412 provided at the center of the bubble removing part 410 and an inclined surface 414 extended from the circumference of the flat surface 412 and connected to the top inner surface of the microfluidic chip 400. If the side surface of the bubble removing part 410 is configured of the inclined surface 414 like this, since bubbles may be moved toward the top of the fluid channel 240 along the inclined surface 414, the bubbles can be more easily moved and arranged to the peripheral space of the bubble removing part 410.

Although it is not shown in FIGS. 3 and 4, according to embodiments, the bubble removing part 310 and 410 may further include a bubble collection part formed by depressing the top inner surface of the substrate 210 toward the top along the circumference of the bubble removing part 310 and 410. Since the bubble collection part is positioned at a relatively higher side of the fluid channel 240 compared with the areas other than the bubble collection part, the bubbles pushed from the bubble removing part 310 and 410 may be collected in the bubble collection part.

According to an embodiment of the present invention, an analysis device may be provided. The analysis device may include the microfluidic chip 200, 300, 400 and 500 according to an embodiment of the present invention described above with reference to FIGS. 2 to 5 and a light measurement module. The light measurement module is a device for radiating light on the microfluidic chip 200, 300, 400 and 500 to measure a reaction product or the like in the microfluidic chip 200, 300, 400 and 500 and detecting an optical signal emitted from the light measurement area, and various light measurement modules applicable in the art can be used. For example, the light measurement module may include a light source arranged to provide light to the fluid channel of the microfluidic chip 200, 300, 400 and 500 and a light detection part arranged to receive the light emitted from the fluid channel, and the light source and the light detection part may be arranged with intervention of the fluid channel (transmissive type) therebetween, or both of them may be arranged at one side of the fluid channel 240 (reflective type).

Figure 5:
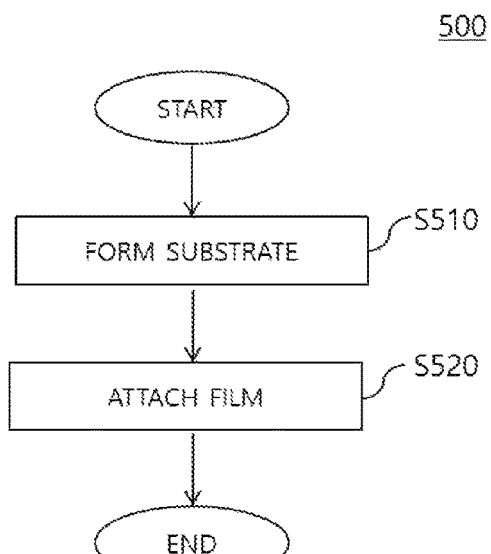
FIG. 5 shows a manufacturing method of a microfluidic chip according to an embodiment of the present invention.
Figure 6:
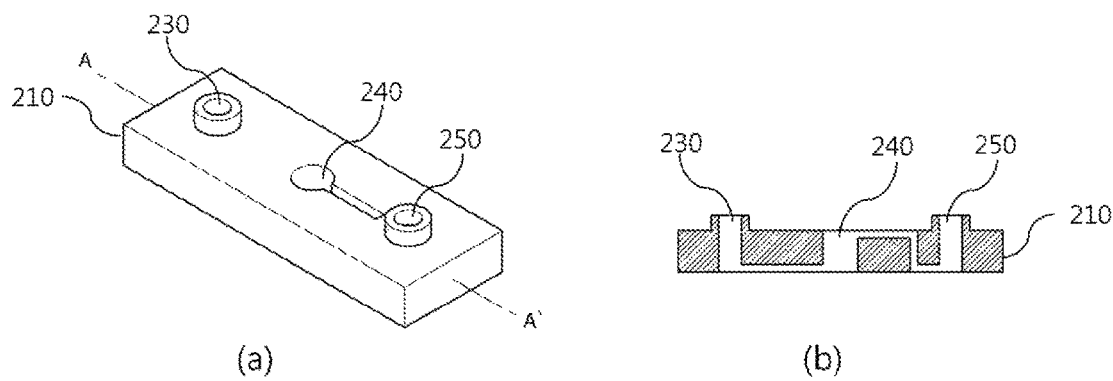
FIGS. 6 and 7 show the steps of a manufacturing method of a microfluidic chip according to an embodiment of the present invention.
Figure 7:
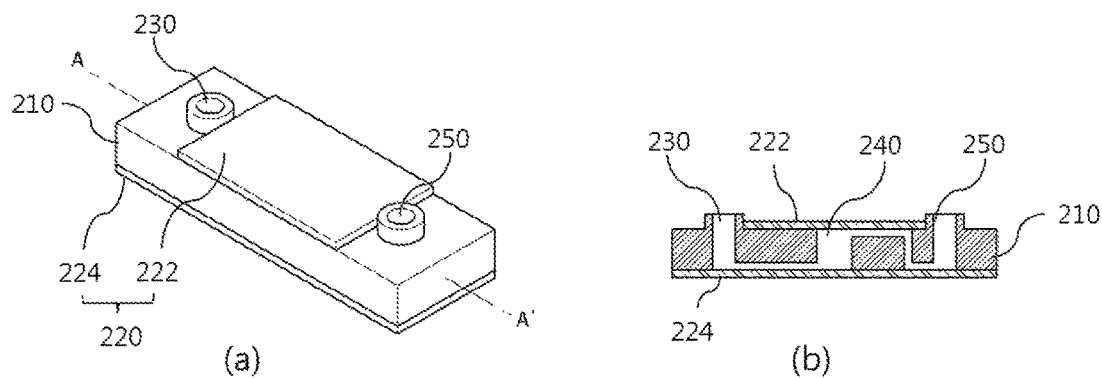

FIG. 5 shows a manufacturing method of a microfluidic chip according to an embodiment of the present invention, and FIGS. 6 and 7 show the steps of a manufacturing method of a microfluidic chip according to an embodiment of the present invention.

The method shown in FIG. 5 is a method of manufacturing the microfluidic chip 200, 300 and 400 shown in FIGS. 2 to 4, and the manufacturing process of FIGS. 6 and 7 is described below based on the method shown in FIG. 5.

First, referring to FIG. 5, a substrate 210 including an inflow part 230, a fluid channel 240 and an outflow part 250 may be formed (step S510). In relation to this, FIG. 6(a) shows a perspective view of the substrate 210 including the inflow part 230, the fluid channel 240 and the outflow part 250, and FIG. 6(b) shows a cross-sectional view of A-A' direction of the substrate 210 shown in 6(a). As shown in the figure, the inflow part 230, the fluid channel 240 and the outflow part 250 of the substrate 210 may be formed to be depressed from the surface (i.e., the top surface and the bottom surface) of the substrate 210 or to penetrate the substrate 210.

Step S510 may be performed using various manufacturing techniques applicable in the art. In an embodiment, step S510 may be performed by etching the surface of the substrate 210, and various etching techniques such as a mechanical method, a chemical method and the like may be used for the etching. In an embodiment, step S510 may be performed by various molding techniques such as injection molding, compression molding and the like.

Subsequently, a film 220 may be attached on the surface of the substrate 210 (step S520). In relation to this, FIG. 7(a) shows a perspective view of the substrate 210 and the film 220 attached on the surface of the substrate 210, and FIG. 7(b) shows a cross-sectional view of A-A' direction of the substrate 210 and the film 220 shown in FIG. 7(a). Referring to FIGS. 7(a) and 7(b), step S520 may be performed by attaching a film 222 on the top surface of the substrate 210 and attaching a film 224 on the bottom surface of the substrate 210, and therefore, at least some of the inflow part 230, the fluid channel 240 and the outflow part 250 formed on the substrate 210 at step S510 may be insulated from the outside. Step S520 may be performed by various bonding methods applicable in the art, such as thermal bonding, ultrasonic bonding, ultraviolet bonding, solvent bonding, tape bonding and the like.

The shapes and structures of the microfluidic chip shown in FIGS. 6 and 7 are only exemplary, and microfluidic chips of various shapes and structures may be used according to embodiments to which the present invention is applied.

As described above, the optimum embodiments have been disclosed in the drawings and the specification. Although the specific terms have been used herein, they have been used merely for the purpose of describing the present disclosure, and have not been used to limit the meanings thereof and the scope of the present disclosure set forth in the claims. Therefore, it will be understood by those having ordinary knowledge in the art that various modifications and other equivalent embodiments can be made. Accordingly, the true technical protection range of this disclosure should be defined by the technical spirit of the attached claims.

The invention claimed is:

1. A microfluidic chip comprising:
a substrate comprising, an inflow part penetrating the substrate in a thickness direction,
an outflow part penetrating the substrate in the thickness direction, and
a fluid channel defined to connect the inflow part and the outflow part and extending in a first direction within the substrate, wherein the thickness direction and the first direction are different from one another; and
a film attached to the substrate and covering at least a portion of at least one of the inflow part, the outflow part, and the fluid channel, the film configured to protect at least one of the inflow part, the outflow part and the fluid channel from the outside;
wherein the film includes a first film attached to a top surface of the substrate and a second film attached to a bottom surface of the substrate;
wherein the fluid channel includes an upper fluid channel formed on a top surface of the substrate; a lower fluid channel formed on a bottom surface of the substrate; and a third fluid channel connecting the upper fluid channel and the lower fluid channel,
wherein a thickness of the at least one film is smaller than a thickness of the substrate.

2. The microfluidic chip of claim 1, wherein the third fluid channel is a chamber.

3. The microfluidic chip of claim 1, wherein the third fluid channel has a first via-hole and a second via-hole, and wherein a width of the first via-hole is greater than a width of the second via-hole.

4. The microfluidic chip of claim 1, wherein the fluid channel comprises at least one of a branch channel and a combined channel by having at least one of the first fluid channel and the second fluid channel or a combination thereof.

5. The microfluidic chip of claim 3, wherein the fluid channel includes a concentration gradient channel which is comprised of at least one of the branch channel and the combined channel, or a combination thereof.

6. The microfluidic chip of claim 1, wherein the fluid channel comprises a bubble removing part, and wherein the bubble removing part is comprised of a light transmissive material, and is protruded in a direction from the first surface to the second surface of the substrate to guide bubbles in a fluid to a predetermined area in the fluid channel.

7. The microfluidic chip of claim 6, wherein the bubble removing part comprises at least one of a flat surface and an inclined surface, wherein the flat surface is disposed at a center of the bubble removing part, and the inclined surface is extended in a direction from a portion of the bubble removing part to the first surface.

8. The microfluidic chip of claim 6, wherein the microfluidic chip further comprises a bubble collection part which has a concave area and is disposed adjacent to the bubble removing part.

9. The microfluidic chip of claim 1, wherein at least a portion of the at least one film is gas permeable.

10. An analysis device comprising:
a microfluidic chip comprising:
a substrate comprising,
an inflow part penetrating the substrate in a thickness direction,
an outflow part penetrating the substrate in the thickness direction, and
a fluid channel defined to connect the inflow part and the outflow part and extending in a first direction within the substrate, wherein the thickness direction and the first direction are different from one another, wherein the fluid channel includes an upper fluid channel formed on a top surface of the substrate; a lower fluid channel formed on a bottom surface of the substrate; and a third fluid channel connecting the upper fluid channel and the lower fluid channel; and
a film attached to the substrate and covering at least a portion of at least one of the inflow part, the outflow part, and the fluid channel, the film configured to protect at least one of the inflow part, the outflow part and the fluid channel from the outside;
wherein the film includes a first film attached to a top surface of the substrate and a second film attached to a bottom surface of the substrate;
wherein a thickness of the at least one film is smaller than a thickness of the substrate; and
a light detection assembly detecting an optical signal emitted from a light measurement area of the microfluidic chip by radiating a light on the microfluidic chip to measure a reaction product in the microfluidic chip.

11. A method of manufacturing a microfluidic chip, the method comprising the steps of:
forming a substrate having
an inflow part penetrating the substrate in a thickness direction,
an outflow part penetrating the substrate in the thickness direction, and
a fluid channel defined to connect the inflow part and the outflow part and extending in a first direction within the substrate, wherein the thickness direction and the first direction are different from one another, wherein the fluid channel includes an upper fluid channel formed on a top surface of the substrate; a lower fluid channel formed on a bottom surface of the substrate; and a third fluid channel connecting the upper fluid channel and the lower fluid channel;
depressing the fluid channel by at least a portion of at least one of a first surface or a second surface of the substrate; and attaching a film to the substrate to cover and protect at least a portion of at least one of the inflow part, the outflow part, and the fluid channel, wherein a thickness of the at least one film is smaller than a thickness of the substrate and wherein the film includes a first film attached to a top surface of the substrate and a second film attached to a bottom surface of the substrate.

12. The microfluidic chip of claim 11, wherein the third fluid channel is a chamber.

13. The microfluidic chip of claim 11, wherein the fluid channel comprises a bubble removing part, and wherein the bubble removing part is comprised of a light transmissive material, and is protruded in a direction from the first surface to the second surface of the substrate to guide bubbles in a fluid to a predetermined area in the fluid channel.

14. The method of claim 13, wherein the bubble removing part comprises at least one of a flat surface and an inclined surface, wherein the flat surface is disposed at a center of the bubble removing part, and the inclined surface is extended in a direction from a portion of the bubble removing part to the first surface.

15. The method of claim 13, wherein the microfluidic chip further comprises a bubble collection part which has a concave area and is disposed adjacent to the bubble removing part.

16. The microfluidic chip of claim 11, wherein at least a portion of the at least one film is gas permeable.

17. The microfluidic chip of claim 11, wherein the fluid channel comprises at least one of a branch channel and a combined channel by having at least one of the first fluid channel and the second fluid channel or a combination thereof.

18. The method of claim 17, wherein the fluid channel includes a concentration gradient channel which is comprised of at least one of the branch channel and the combined channel, or a combination thereof.

* * * * *